United States Patent [19]

Hughes, Jr. et al.

[11] 3,977,411
[45] Aug. 31, 1976

[54] CARDIAC PACER SYSTEM AND METHOD

[75] Inventors: Howard C. Hughes, Jr., Cornwall; Robert R. Brownlee, State College; G. Frank O. Tyers, Hershey, all of Pa.

[73] Assignee: Research Corporation, New York, N.Y.

[22] Filed: June 12, 1975

[21] Appl. No.: 586,169

[52] U.S. Cl. .............................. 128/419 P; 128/404
[51] Int. Cl.² ............................................ A61N 1/36
[58] Field of Search ............... 128/404, 418, 419 P, 128/419 PG, 419 PT

[56] References Cited
UNITED STATES PATENTS

| | | | |
|---|---|---|---|
| 3,625,201 | 12/1971 | Murphy, Jr. | 128/419 PT |
| 3,842,843 | 10/1974 | Mourot et al. | 128/419 P |
| 3,857,398 | 12/1974 | Rubin | 128/419 P |
| 3,893,461 | 7/1975 | Preston | 128/419 P |

*Primary Examiner*—William E. Kamm
*Attorney, Agent, or Firm*—Cooper, Dunham, Clark, Griffin & Moran

[57] ABSTRACT

A cardiac pacer system includes a first relatively large contact area electrode for sensing cardiac activity and a second electrode of substantially smaller contact area than the first to apply artificial stimulating pulses to the heart. The first electrode has a sufficiently large contact area to achieve a relatively high sensitivity to cardiac activity and the second electrode has a sufficiently small contact area to generate a relatively high current density at the electrode-tissue interface when the artificial stimulating pulses are applied to the heart. The electrodes are supported in a spaced relationship by an electrically insulating spacer. Each electrode may be directly wired to an appropriate point within the cardiac pacer, and referenced to a common electrical return point by means of a third, common electrode. Alternatively, the first and second electrodes may be connected to the pacer with a single lead, with suitable decoupling circuitry between the single lead and each electrode. The third or common electrode may be eliminated by having the first and second electrodes each serve as a common electrode for the other, while employing suitable decoupling circuitry between the pacer and the electrodes.

9 Claims, 4 Drawing Figures

CARDIAC PACER SYSTEM AND METHOD

BACKGROUND OF THE INVENTION

This invention relates to cardiac pacers, and relates more particularly to an improved system in which both the sensing and pacing functions are enhanced.

It has been recognized that the energy requirements for cardiac pacing can be decreased by reducing the contact surface area of the pacing electrode. The improved performance of the small contact area pacing electrode results from the generation of a relatively high current density at the electrode-tissue interface for a given energy input. Various commercially available electrodes having relatively small contact areas have been developed to take advantage of this phenomenon. However, it has been found that by decreasing the contact area of the pacing electrode, its ability to sense electrical activity of the heart is reduced. This sensing of cardiac electrical activity is a necessary function in all programmed pacers to prevent competitive pacing and the possibility of cardiac decompensation and ventricular fibrillation.

Heretofore, the sensing problems associated with small contact area electrodes have been compensated for in two ways. One prior art approach has been to increase the sensitivity of the associated pacer sensing circuitry to compensate for the reduced sensitivity of the smaller electrode. A second approach has been to simply increase electrode size. However, if the sensitivity of the pacer electronics is increased, sensitivity to contaminating electrical fields and other interference sources is correspondingly increased. Sensitivity to external interference increases the risk of arrhythmia and may cause serious medical complications. On the other hand, simply increasing electrode size improves the sensing ability of the electrode, but the advantages inherent in a small contact area electrode, namely high current density and decreased energy requirements, are compromised.

While it has thus been recognized that a small contact area electrode is desirable for optimal pacing, a workable system for overcoming the disadvantages associated with using such an electrode for sensing has not heretofore been developed. Accordingly, there is a well-defined need for an electrode system in which both the sensing and pacing functions are enhanced.

Representative prior art electrode systems having electrode contact areas of different sizes are shown in U.S. Pat. Nos. 3,253,595 and 3,815,611. Neither of these references discloses a system in which both sensing and pacing functions are enhanced, however. The general concept of utilizing an electrode in conjunction with an electrical decoupling network is shown in U.S. Pat. No. 3,625,201. None of these references shows or suggests the novel electrode system disclosed herein. Similarly, currently available small contact area electrode systems, which utilize the smaller electrode for both pacing and sensing, do not enhance both the sensing and pacing functions.

SUMMARY OF THE INVENTION

An object of this invention is to provide a cardiac pacer in which both the sensing and pacing functions are enhanced.

It is a further object of this invention to provide a system which has a relatively high sensitivity to cardiac activity and which is capable of generating a relatively high current density at the electrode-tissue interface when artificial stimulating pulses are applied to the heart.

Still another object is to provide a system which has a decreased energy requirement in the pacing mode.

To these and other ends, one embodiment of the present invention contemplates a system for use in a cardiac pacer of the type having a sensing input for receiving an input signal representing cardiac activity and a pulse generator output responsive to the input signal to provide artificial heart stimulating pulses for application to the heart. The system includes a first electrode having a relatively large contact area for sensing cardiac activity. This first electrode, which has a sufficiently large contact area to achieve a relatively high sensitivity to cardiac activity, is connected to the sensing input of the cardiac pacer. A second electrode, of substantially smaller contact area than the first, is connected to the pulse generator output of the cardiac pacer and couples the artificial heart stimulating pulses to the heart. The contact area of the second electrode is sufficiently small to generate a relatively high current density at the electrode-tissue interface when the artificial stimulating pulses are applied.

DETAILED DESCRIPTION

Figure 1:
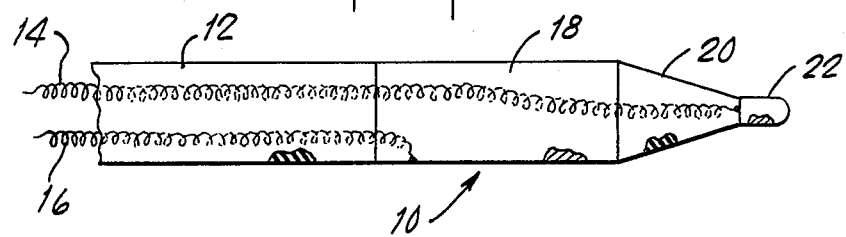
FIG. 1 is a diagram of an electrode tip for use in an electrode system in accordance with the invention.

Referring to FIG. 1 of the drawings, there is shown an electrode tip suitable for use in the disclosed invention, generally identified by reference numeral 10. The electrode tip 10 has a small contact area cylindrical electrode 22 and a larger contact area ring electrode 18 separated therefrom by a flexible nonconductive material 20. Electrodes 18 and 22 are connected to conductors 16 and 14, respectively, and these conductors are insulated by a flexible nonconductive material 12.

In the illustrative embodiment of FIG. 1, smaller electrode 22 is positioned at the tip end of the electrode. Non-conductive material 20 serves as an interelectrode insulator as well as a smoothly-tapered mechanical spacer between smaller electrode 22 and larger electrode 18. In this embodiment, electrode 18 is shown as a cylindrical annular conductor while electrode 22 is shown as a solid cylindrical conductor. The electrodes are connected to the cardiac pacer by conductors 14 and 16, which may be coiled wires or leads to improve flexural strength. Leads 14 and 16 are insulated by a covering 12 which may be of a suitable body-compatible flexible nonconductive material. While the contact area dimensions of the electrodes are of considerable importance to the invention, the details of construction are not critical, and the electrode tip illustrated in FIG. 1 is accordingly to be considered as an illustrative configuration.

In order to optimize the pacing function, it has been found that smaller electrode 22 should have a contact surface area of less than about 20 mm² but greater than about 5 mm². The smaller electrode may be of a cylindrical configuration, as shown, or of a ball tip or other configuration, since it is the contact area which is of primary importance. For optimal sensing, the larger electrode should have a contact area of greater than about 75 mm² but less than about 200 mm². As in the case of the smaller electrode, it is the contact area rather than the exact diameter or shape of the electrode that is most significant.

Figure 2:
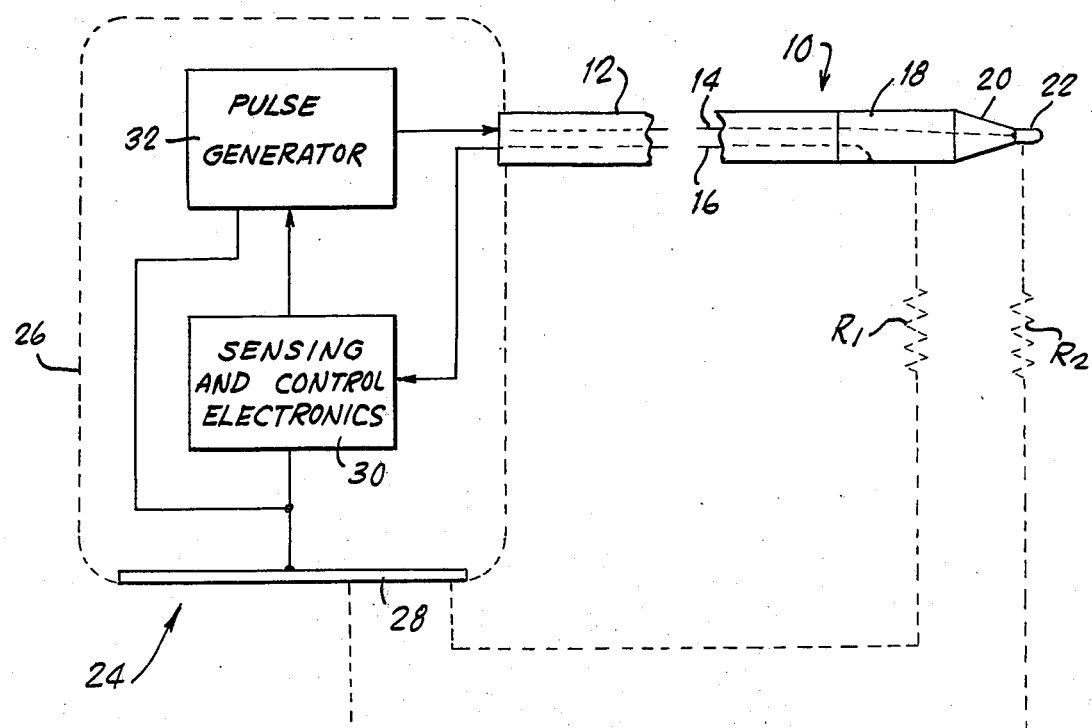
FIG. 2 is a block diagram of a cardiac pacing apparatus having an electrode system in accordance with the invention.

In FIG. 2, there is shown a cardiac pacing apparatus, generally identified by reference numeral 24, which utilizes the electrode configuration of FIG. 1. Electrode tip 10 is electrically connected to the electronics of cardiac pacer 24 by leads 14 and 16. Larger electrode 18, which performs the sensing function, is connected by lead 16 to the input of a sensing and control electronics block 30, which receives an input signal from the electrode and produces a control signal output as a function of the received signal. The output of block 30 is fed to a pulse generator 32 which generates artificial heart stimulating pulses in response to the control signal. These artificial heart stimulating pulses are coupled to smaller electrode 22 by lead 14. Leads 14 and 16 are insulated from each other by flexible nonconductive material 12, and electrodes 18 and 22 are similarly insulated by nonconductive material 20, as discussed above.

An electrical return point on pulse generator 32 and a corresponding electrical return point on sensing and control electronics 30 are connected together to form a common return or reference point for the pacing electronics, and this common point is electrically connected to an external conductive portion 28 of a pacer enclosure 26. Conductive portion 28, which may be a metallic plate or the like, functions as a common or indifferent electrode, and this third electrode provides a return path for electrodes 18 and 22. This is illustrated schematically in FIG. 2 by resistors R1 and R2, shown connected respectively between electrodes 18 and 28 and between electrodes 22 and 28. Resistors R1 and R2 represent the electrical tissue resistance appearing between each tip electrode and the common electrode when the cardiac pacing apparatus is implanted.

The configuration described above provides a sensing circuit and a pacing circuit. The sensing input circuit is formed by sensing electronics 30, lead 16, electrode 18, body resistance R1, common electrode 28 and the return connection to electronics 30. Similarly, the pacing circuit for artificial heart stimulating pulses generated by pulse generator 32 includes the pulse generator, lead 14, electrode 22, body resistance R2, common electrode 28 and the pulse generator return connection. Since the sensing and pacing functions are accomplished by different electrodes, the contact area of each electrode may be selected to optimize its particular function. In conventional electrode systems, on the other hand, even when variously-sized electrodes are provided, the smaller electrode is used for both sensing and pacing, so that optimization for both functions is impossible.

Figure 3:
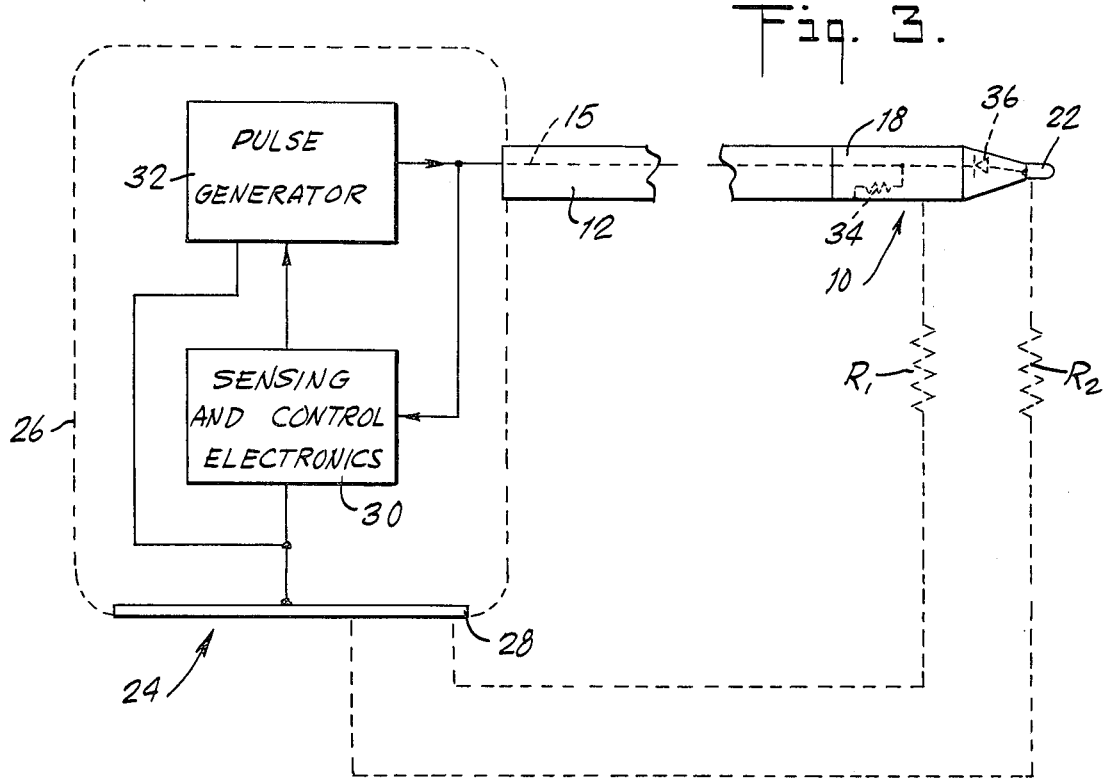
FIG. 3 is a block diagram of a cardiac pacing apparatus showing an alternative embodiment of the electrode system.

An alternative embodiment of the system is shown in FIG. 3. In this embodiment, the output of pulse generator 32 and the input of sensing electronics 30 are connected together within enclosure 26, and the common electrical point formed thereby is connected to the electrode tip 10 by a single lead 15 rather than by a pair of wires. Smaller electrode 22 is connected to lead 15 by diode 36, and larger electrode 18 is connected to lead 15 by resistor 34, as shown in FIG. 3.

For pacing, a negative pacing pulse is supplied from pulse generator 32 through lead 15 and is coupled to smaller electrode 22 through diode 36, which is connected with appropriate polarity to conduct a negative pulse to the electrode. In order to minimize the voltage drop associated with the insertion of a series-connected diode in the pacing circuit, diode 36 may advantageously be a hot carrier diode, such as a 1N5711 or the like. Diodes of this type are characterized by a forward voltage drop in the order of 0.3–0.4 volts, and are thus particularly suited for this application. In order to avoid reducing the current density at smaller electrode 22, resistor 34 is inserted between lead 15 and larger electrode 18. If the value of resistor 34 is made large relative to the resistance at the electrode-tissue interface of smaller electrode 22, then relatively little current will be shunted away from the smaller electrode pacing circuit.

For sensing, signals detected by larger electrode 18 are coupled through resistor 34 and lead 15 back to sensing and control electronics 30. In order to minimize losses in this signal path, the resistance of resistor 34 must be substantially lower than the input impedance of block 30. Sensed signals coupled from the larger electrode to lead 15 by resistor 34 are isolated from the smaller electrode by diode 36, in order to minimize loading effects. It has been found that resistance values of between about 1500 ohms and 4000 ohms are suitable for satisfying the conditions indicated above. As in the previous embodiment, conductive plate 28 serves as a common electrode for sensing and pacing.

The principal advantage of the system shown in FIG. 3 resides in the use of a single electrode lead rather than a dual-lead configuration, thus reducing complexity and enabling the use of a single-contact connector at the pacer electronics housing. This advantage is obtained at the expense of slightly decreased efficiency as compared to the dual-lead system of FIG. 2, as well as somewhat reduced noise immunity due to the requirement for somewhat higher impedance levels in the sensing amplifier.

Figure 4:
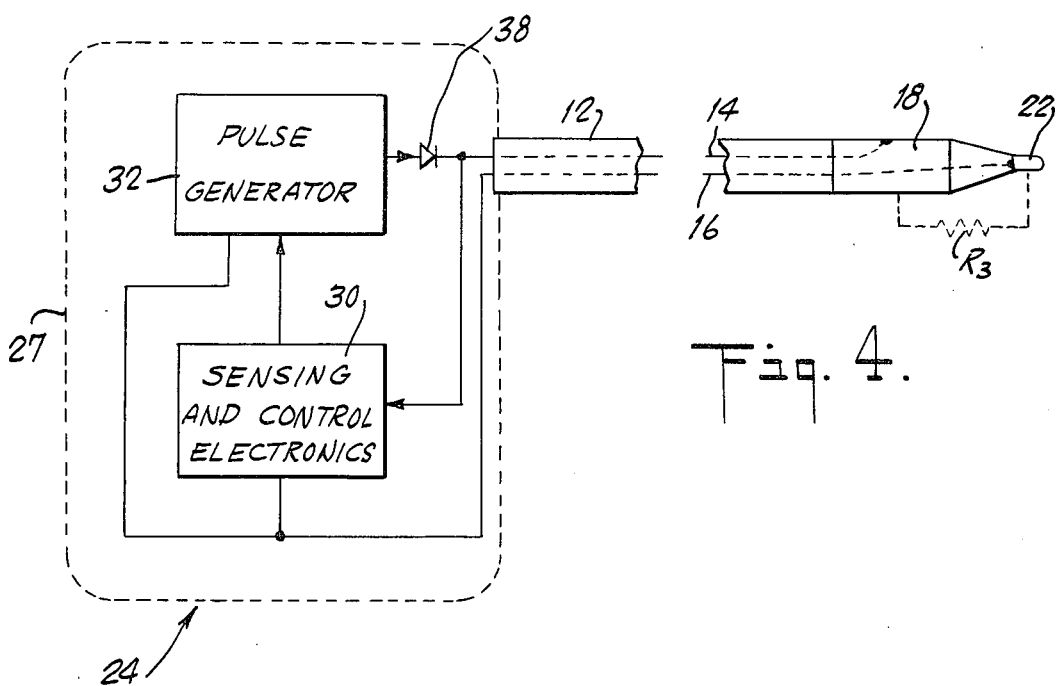
FIG. 4 is a block diagram of a cardiac pacing apparatus showing a second alternative embodiment of the invention.

Another alternative system is shown in FIG. 4. In this configuration, the enclosure 24 comprises a nonconductive housing 27 having no electrode portion. An electrical return point on pulse generator 32 and a corresponding return point on sensing and control electronics 30 are connected together to form a common electrical return point within the pacer housing. This common point is connected to electrode lead 16, which is in turn connected directly to smaller electrode 22. The output of pulse generator 32 is coupled through a diode 38 to wire 14, which is connected directly to larger electrode 18, while the input of sensing and control electronics 30 is connected directly to wire 14. The effective tissue resistance between electrodes 18 and 22 is represented in FIG. 4 by a resistor R3, and diode 38 may be a hot carrier diode, such as a 1N5711 or the like.

For pacing, a positive pulse output from pulse generator 32 is coupled through diode 38, with polarity as shown, and through wire 14 to larger electrode 18. Larger electrode 18 is driven through diode 38 as the positive electrode, while a high pacing current density is developed at smaller negative electrode 22, which is coupled back to the common return point through lead 16. Thus, in effect, larger electrode 18 serves as an indifferent electrode for pacing.

For sensing, larger electrode 18 serves as the cardiac monitor, and couples signals directly to sensing and control electronics 30 through lead 14, while smaller electrode 22 serves in effect as an indifferent electrode. It is thus possible to eliminate the third electrode 28, shown in FIG. 2 and FIG. 3.

It has been found that the use of a larger electrode in combination with a smaller electrode for sensing does not degrade sensing performance as compared to the use of two larger electrodes. The apparent explanation for this phenomenon is that with differently sized electrodes, the smaller electrode performs adequately as an indifferent electrode for the larger electrode, so that sensitivity is not reduced by reducing the contact area of one electrode. Furthermore, it appears that there may be an advantage to using this configuration for sensing purposes. When two equally large contact area electrodes are employed in fairly close proximity, as in some present bipolar leads, in-phase signals are developed on each electrode, resulting in reduced sensitivity due to cancellation. With differently sized electrodes, less cancellation appears to take place due to the unequal voltages developed on the two electrodes, thus apparently resulting in an improved signal-to-noise ratio. It has been found that this cancellation effect may be realized in the configuration of FIG. 4 with an interelectrode spacing between electrodes 18 and 22 of about 5 to 50 millimeters.

We claim:

1. A system for use in a cardiac pacer of the type having control means for receiving an input signal representing cardiac activity and for producing a control signal in accordance therewith, and pulse generating means responsive to said control signal for generating artificial heart stimulating pulses for application to the heart, which system comprises:
    first electrode means for sensing cardiac activity, operatively connectable to said control means to provide an input signal representing cardiac activity thereto and having a large contact area to enhance sensitivity to cardiac activity;
    second electrode means of substantially smaller contact area than said first electrode means, operatively connectable to said pulse generating means, for receiving said artificial heart stimulating pulses from said pulse generating means and applying said pulses to the heart tissue, said second electrode means generating a high current density at its electrode-tissue interface when said artificial stimulating pulses are applied to the heart; and
    electrically insulating means for supporting said electrodes in a spaced relationship.

2. A system as in claim 1 wherein said first electrode means for sensing cardiac activity has a contact area of greater than about 75 mm$^2$ but less than about 200 mm$^2$ and said second electrode means for applying artificial pulses to the heart has a contact area of less than about 20 mm$^2$ but greater than about 5 mm$^2$.

3. A system as in claim 1, further comprising:
    first conductor means directly connecting said first electrode means to said control means, for conducting an input signal representing cardiac activity from said first electrode means to said control means;
    second conductor means directly connecting said second electrode means to the output of said pulse generating means, for conducting said artificial heart stimulating pulses from said pulse generating means to said second electrode means;
    an electrical return point common to said control means and said pulse generating means; and
    third electrode means for referencing said first and second electrode means to said electrical return point common to said control means and said pulse generating means, said third electrode means being directly connected to said common return point.

4. A system as in claim 3, further comprising an enclosure means having a conductive portion for housing said control means and said pulse generating means, and wherein said third electrode means comprises said conductive portion, said conductive portion being electrically connected to said common electrical return point to reference said first and second electrode means to said return point.

5. A system as in claim 1, further comprising:
    a resistor having a first terminal connected to said first electrode means and a second terminal;
    a diode having a first terminal connected to said second electrode means and a second terminal, said second terminals of said resistor and said diode being joined at a first junction and the sensing input of said control means and the output of said pulse generating means being joined at a second junction;
    a single conductor to electrically connect said first junction to said second junction;
    an electrical return point common to said control means and said pulse generating means; and
    third electrode means for referencing said first and second electrode means to said electrical return point common to said control means and said pulse generating means, said third electrode means being directly connected to said common return point.

6. A system as in claim 5, wherein said resistor has a resistance of between about 1500Ω and 4000Ω and wherein said diode is of the hot carrier type and is connected between said electrode means and said first junction with appropriate polarity to present a conductive path for said artificial heart stimulating pulses from said pulse generating means.

7. A system as in claim 1, further comprising:
    a diode having a first terminal connected to the output of said pulse generating means and a second terminal connected to the sensing input of said control means;
    a first conductor to electrically connect said first electrode means to the second terminal of said diode;
    an electrical return point common to said control means and said pulse generating means; and
    a second conductor for electrically connecting said second electrode means to said common return point.

8. A system as in claim 7, wherein said diode is of the hot carrier type and is connected between said pulse generating means and said first conductor with appropriate polarity to present a conductive path for said artificial heart stimulating pulses from said pulse generating means.

9. A method of coupling a cardiac pacer to a patient's heart, which comprises:

sensing cardiac activity and generating an input signal proportional thereto with a first electrode having a large contact area to enhance sensitivity to cardiac activity;

applying said input signal to said cardiac pacer to control the generation of artificial heart stimulating pulses thereby; and applying said artificial heart stimulating pulses to the heart with a second electrode of substantially smaller contact area than said first electrode to achieve a high application current density.

* * * * *